United States Patent [19]

Kandel et al.

[11] 4,241,734
[45] Dec. 30, 1980

[54] DEVICE FOR PUTTING CLIPS ON BLOOD VESSELS

[76] Inventors: Eduard I. Kandel, ulitsa Alexeya Tolstogo, 22/2, kv. 75; Vyacheslav V. Peresedov, Teply stan, 3 mikroraion, korpus 37, kv. 303, both of Moscow, U.S.S.R.

[21] Appl. No.: 963,677

[22] Filed: Nov. 27, 1978

[51] Int. Cl.³ .............................................. A61B 17/12
[52] U.S. Cl. ................................................... 128/325
[58] Field of Search ............... 128/325, 346, 321, 347, 128/303 A, 326, 334 R; 72/410; 29/243.56

[56] References Cited

U.S. PATENT DOCUMENTS

| 3,777,538 | 12/1973 | Weatherly et al. | 128/325 X |
| 3,957,055 | 5/1976 | Linder et al. | 128/351 |
| 3,958,576 | 5/1976 | Komiya | 128/346 |
| 3,989,049 | 11/1976 | Yoon | 128/326 |

Primary Examiner—Robert W. Michell
Assistant Examiner—Michael H. Thaler
Attorney, Agent, or Firm—Lackenbach, Lilling & Siegel

[57] ABSTRACT

A device for putting clips on blood vessels comprises a tubular member moving with respect to a shackle and a guide or working rod inserted into the cavity of the tubular member.

The method of treating brain aneurysms consists in that a hole is cut out in the patient's cranium under local anesthesia, a stereotaxic apparatus and the proposed device are installed in the hole, a guide rod is installed in the tubular member of the device, and the latter is brought to the part of the vessel to be clipped. The guide rod is then removed from the tubular member, and the working rod holding the clip is inserted instead. The clip is pushed out from the cavity of the tubular member and the vessel is clipped. The clip is now released from the grip, and the tubular member together with the working rod are removed from the operative hole.

3 Claims, 19 Drawing Figures

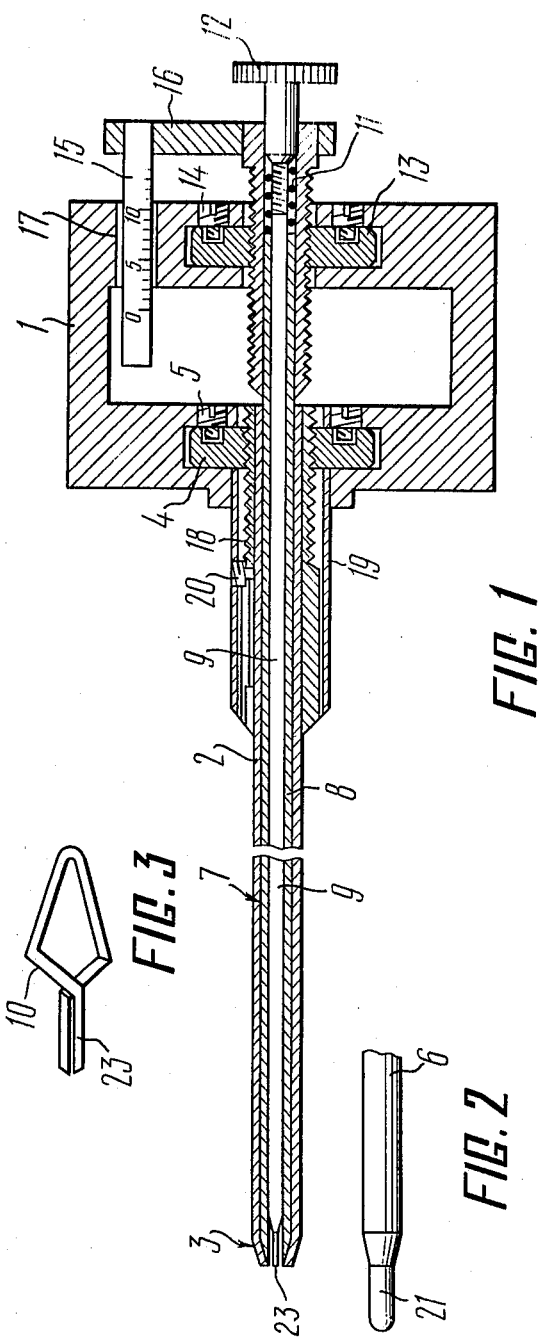

DEVICE FOR PUTTING CLIPS ON BLOOD VESSELS

FIELD OF THE INVENTION

The invention relates to surgical methods of treatment, and more particularly to devices for putting clips on blood vessels and methods of treating cerebral aneurysms with these devices.

The proposed invention can be used in surgical treatment of arterial and arteriovenous aneurysms of the brain by the stereotaxic method, and also for putting clips on various vessels in other operations.

BACKGROUND OF THE INVENTION

Known in the prior art are open stereotaxic operations on arteriovenous aneurysms (Riechert T. and Mundinger E., "J. Neurosurg.", 1964 21,5,358-363). These operations consist in that a patient under a general anesthesia is given a vast bone plastic trepanation on the side of the aneurysm. After opening the dura mater, using stereotaxic calculations and a stereotaxic apparatus, a metal guiding rod with a catheter pulled over it it introduced into the brain to reach a deeply located aneurysm. The stereotaxic apparatus is then withdrawn, and the guiding rod pulled out from the catheter, while the latter remains in the brain. Using a spatula, a well is then made in the brain to reach the aneurysm. The width of the well is 25 mm, and the operation can thus be effected under visual control. Using the known clip-holder, a clip is then adjusted onto the vessel feeding the arteriovenous aneurysm, or the aneurysm is ectomized. The stereotaxic method is thus used only to locate the aneurysm, while all other operations are carried out under visual control using any known clip holders.

Known in the prior art is a device intended to put clips on a cerebral vessel, comprising a shackle with a tubular member there inside, along which changeable rods are moved, viz., a guiding rod and a working rod carrying a two-jaw chuck that grips the clip. Each rod has a rule that moves in the shackle with respect to the guides. The device is used to put clips by the stereotaxic method (cf. USSR Inventors' Certificate No. 452,336).

As the clip appears from the end of the tubular member with its jaws open, it moves forward safely since the clip is in front of the vessel. But as the clip jaws are closed to compress the vessel, the clip must be stationary so as not to injure the vessel. The device should therefore be withdrawn from the brain to a distance equal to the depth of the clip penetration. This synchronous operation is performed by the stereotaxic apparatus, which is thus "double-controlled". This is inconvenient and is fraught with danger of injuring the vessel.

SUMMARY OF THE INVENTION

The invention is aimed at providing a device for putting clips on blood vessels, without causing any damage the vessels during operation of the device.

It is an object of the present invention to provide a method of treating aneurysms of the brain, that will make it possible to apply the stereotaxic method during operation on aneurysms of the brain at the stage of approach to the aneurysm, as well as at the stage of putting clips on a stricken blood vessel.

Another object of the invention is to provide a method of treating aneurysms of the brain using a device for putting clips on the blood vessel that will preclude the rupture of the aneurysm.

Still another object of the invention is to provide a method of treating brain aneurysms that will prevent complications due to the possible rupture of the aneurysm or injured cerebral vessels.

Yet another object of the invention is to provide a method of treating brain aneurysms that will make it possible to remove the clip whenever the patient's conditions is aggravated.

In accordance with these and other objects, the invention resides in a device for putting clips on blood vessels, comprising a shackle and a tubular member thereinside with a guiding or working rod carrying a clip at its one end moving inside said housing, and wherein the tubular member is made movable with respect to the shackle.

It is desirable that, in order to move the tubular member, a threaded sleeve be fixed thereon, the sleeve interacting with an adjusting nut, and another sleeve should also be installed in the shackle coaxially with the former sleeve.

The device can be provided with a fixing device in the form of a screw installed in the second sleeve and interacting with the threaded sleeve, to preclude rotation of one sleeve in relation to the other.

The objects of the invention are also attained by the method of treating brain aneurysms, wherein a hole is cut in the cranium of the patient under a local anesthesia. Then, a stereotaxic apparatus, and the device for putting clips on the vessels are installed in the hole and then, a guiding rod is inserted into the cavity of the tubular member, and the tubular member, together with the guiding rod is moved toward the part of the vessel to be clipped. The guiding rod is then removed and the working rod carrying a clip is inserted into the cavity of the tubular member instead. The clip held by the grip is moved out of the tubular member and the vessel is clipped therewith. The clip is then released from the grip and the tubular member, together with the working rod, are removed from the hole in the cranium.

Whenever it is necessary to remove the clip from the vessel, the working rod is put inside the tubular member, the latter is moved toward the clip, the clip is grasped by the working rod to release the vessel, and the tubular member, with the clip inside its cavity, is finally removed from the brain.

A clip can be moved out of the tubular member either as it is being brought close to the vessel or in the immediate vicinity to the vessel.

BRIEF DESCRIPTION OF THE DRAWINGS

Other objects and advantages of the invention will become more apparent from the following description of an embodiment thereof with reference to the appended drawings, in which:

FIG. 1 shows in a sectional view a device for putting clips on blood vessels, made in accordance with the invention;

FIG. 2 shows part of a guiding rod used with the device of FIG. 1;

FIG. 3 shows a clip;

DETAILED DESCRIPTION OF THE PREFERRED EMBODIMENTS

Figure 4A:
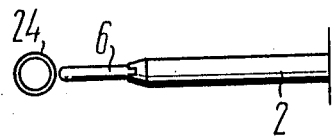
FIGS. 4a, b, c, d, e, f, g, h, i, j, k, and l show various stages of putting a clip on a blood vessel.

The device for putting clips on blood vessels, for example, cerebral vessels, comprises a shackle 1 (FIG. 1), a tubular housing member 2 installed therein, and having a tapered end 3 and moving relative to the shackle 1 by means of an adjusting nut 4. The adjusting nut 4 is fixed in the shackle with screws 5. Either a guiding rod 6 (FIG. 2) or a working rod 7 (FIG. 1) can be placed inside the tubular housing member 2.

The working rod 7 also has a tubular member 8 within which a grip 9 is located. The grip 9 holds the clip 10 (FIGS. 1 and 3) at its end 22. The grip 9 is positioned inside the tubular member 8 of the working rod 7 by a spring 11 controlled by a button 12. Like the guiding rod 6, the rod 7 is also threaded on the outside, the thread interacting with the adjusting nut 13 installed in the shackle 1 and fixed therein with screws 14. The working rod 7 (like the rod 6) has a rule 15 installed on the shank 16 and moving along guides 17 in the shackle 1.

According to the invention, the tubular housing member 2 is made movable with respect to the shackle 1, for which purpose it bears a threaded sleeve 18 interacting with a nut 4, while the shackle 1 has a sleeve 19 installed coaxially with the sleeve 18. In order to prevent rotation of one sleeve relative to the other, they are provided with a fixing screw 20.

The device operates as follows.

In order to minimize injury that otherwise can be done to the brain by the open end of the tubular housing member 2, its hollow is filled with the guide rod 6 (from the side of the shackle 1) with installation of the rule into the guide 17 of the shackle 1. The guide rod 6 is lowered into the brain by rotating the adjusting nut 13. After the guide rod 6 touches on the target with its end 21, the guide rod 6 is removed.

The removable clip 10 is suitably held by the end of the grip 9 and introduced into the hollow of the member 2 through the shackle 1. The working rod 7 is lowered by manipulating the adjusting nut 13.

The clip 10 passes through the tapered end 3 of the tubular housing member 2, and is compressed on the sides to open its jaws 23. The clip 10 is lowered until its jaws 23 are open to a full position. This stage thus consists in lowering the clip 10 and opening its jaws 23.

The adjusting nut 4 is now rotated. It interacts with the sleeve 18 to move the tubular housing 2 and the sleeve 18 with respect to the sleeve 19 of the shackle 1. The tubular housing 2 is thus withdrawn. The end 3 of the tubular housing member 2 moves toward the end of the loop of the clip 10 and its jaws 23 are closed by the resilient force of the clip loop. The clip now compresses the vessel.

The clip remains motionless at this stage of the operation. The button 12 is now pressed on to suitably open the grip 9 and to release the clip 10. The device is then withdrawn from the field of operation.

Whenever it is necessary to remove the clip from the blood vessel, the tubular housing member 2 is lowered by rotating the adjusting nut 13. The tapered end of the tubular housing member 2 moves onto the clip 10 to compress its loop and to release the vessel. The adjusting nut 14 is now rotated in the reverse direction to pull the clip 10 by the working rod 7 into the tubular housing member 2.

The method of treating brain aneurysms consists in the following.

Using pre-operative frontal and lateral angiograms, a target point is determined on the vessel leading to the arteriovenous aneurysm, or on the neck of an arterial aneurysm. In the case of arteriovenous aneurysms, the target point on the feeding vessel is beyond the last normal branch of this vessel in the distal direction. In arterial aneurysms, depending on the length of the neck, the point is located at a distance of 10 to 15 mm away from the vessel. Using the angiogram, the diameter of the vessel (neck of the aneurysm) is determined at the target point and its outer diameter is calculated. The size of the clip is now selected so that the width of the gap between its open jaws should exceed the outer diameter of the vessel by 1.5 to 2 mm. The chosen clip is now loaded into the device and the width to which the clip jaws 23 should be opened is set on the rule 15. Taking into account the functional importance of the brain structures through which the device will pass, a site is selected on the cranium where the operative hole will be cut out. A sagittal line is drawn on the patient's cranium, the point of intersection with the coronary suture is determined, the center of the hole is marked, and the line passing through the plane where the clip will be opened is determined.

The operation is effected under a local anesthesia. A catheter is inserted into the common or internal carotid artery to carry out angiography during the operation. A sagittal incision 4 to 5 cm long passing through the marked center is made on the skin, and a hole 25 mm in diameter is made in the shall with a crown-shaped cutter. Dura mater is now cut, and the stereotaxic apparatus is fixed in the cut out hole.

Figure 4G:
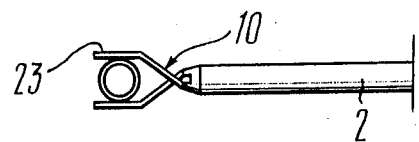
Figure 4B:
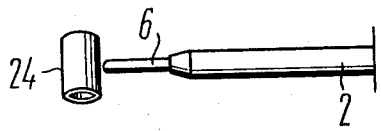
Figure 4H:
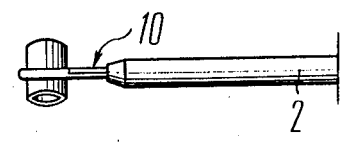
Figure 4C:
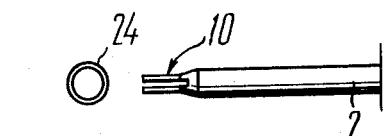

A guide rod 6 is passed into the cavity of the tubular member 2 (FIGS. 4a, b). The length of the end of the guide rod 6 that emerges from the tubular housing member 2 should be equal to the distance from the end of the tubular housing member 2 to the ends of the clip jaws 23 (FIG. 3) opened to the full extent. The proposed device is now installed into the stereotaxic apparatus and oriented in the required plane where the clip jaws 23 will be separated. The patient's head is fixed rigidly. The proposed device is introduced partly into the brain in the direction of the target point, and angiography in two projections is made. The target point of the pre-operative angiogram is transferred onto the newly obtained angiogram. Using regular stereotaxic calculations, the end of the guide rod 6 (FIGS. 4a, b) is moved to the vessel 24. The guide rod 6 is now pulled out and the working rod 7 (FIGS. 4c, d) is installed in place thereof. The grip 9 of the working rod 7 carries the clip 10. The clip jaws 23 (FIGS. 4e, f) are set apart to the maximum extent, and the entire device is lowered to a distance equal to the diameter of the vessel 24 (FIGS. 4g, h). (The open clip embraces the vessel 24).

Figure 4I:
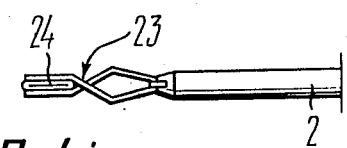
Figure 4D:
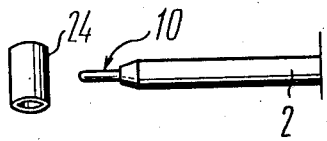
Figure 4J:
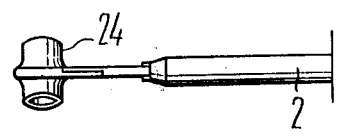

Angiography in two projections is now made to check the position of the clip on the vessel. The clip is then released (FIGS. 4i, j) and the compression of the vessel (or the aneurysm neck) is checked angiographically. The clip is now fully unloaded from the device (FIGS. 4k, l) and the latter is withdrawn from the brain. The cut out bone is replaced and the wound sutured.

Figure 4E:
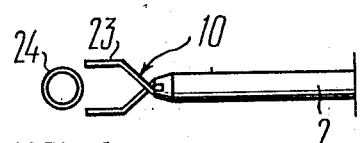
Figure 4K:
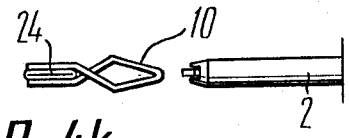
Figure 4F:
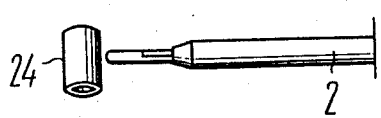
Figure 4L:
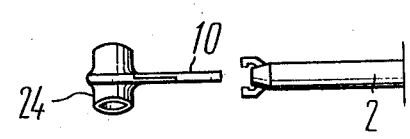

If it is necessary to remove the clip, the tubular housing member 2 with the working rod 7 there inside, is moved toward the clip 10 (FIGS. 4k, l) on the vessel 24, the clip 10 is captured by the end of the grip 0 of the working rod 7 (FIGS. 4,i,j), the jaws 23 are opened (FIGS. 4g,h) by moving the working rod, and the vessel 24 is released (FIGS. 4e, f). The clip 10 is pulled inside the tubular housing member 2 (FIGS. 4c,d), and the tubular housing member 2 together with the working rod 7 are removed from the brain.

Figure 5A:
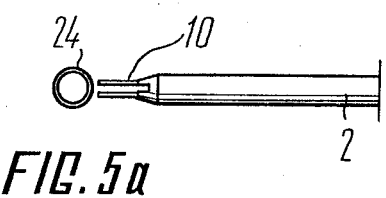
FIGS. 5a, b, c, and d, show various stages of putting a clip on a blood vessel with the clip opening in the immediate vicinity of a blood vessel.
Figure 5B:
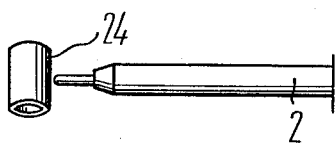
Figure 5C:
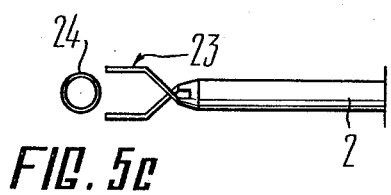
Figure 5D:
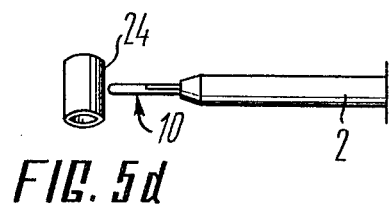

The clip 10 can be either brought to the vessel in the open position as shown in FIG. 4 or first lowered close to the vessel 24 (FIGS. 5a, b) and then its jaws opened (FIGS. 5c, d).

The invention prevents injury to the vessel that otherwise is possible during repeated reciprocations of the clip as it compresses the vessel. The invention accelerates the process of putting a clip on a blood vessel and simplifies the control of the device is operation.

The device has been tried in experiments on animals. Carotid and femoral arteries were isolated on experimental animals (dogs) under a morphine-hexenal anesthesia and were clipped with the proposed device. The degree of compression of the vessels was controlled by applying a forceps onto the same vessel, a small distance from the clip in the distal direction, with subsequent puncture of the confined part of the vessel and suction of the blood there from.

We carried out 15 experiments on vessels 1 to 4.5 mm in diameter to try clips of the corresponding size. The vessels were securely clipped in each case and no damage was done to the vessels walls.

The proposed device and the method were tried clinically.

Fifteen operations of stereotaxic clipping of the vessels feeding aneurysms were carried out on 13 patients with radically inoperable arteriovenous aneurysms of the hemispheres. The aneurysms were fed with blood from the system of anterior, median, and posterior cerebral arteries. Eight stereotaxic operations of clipping the neck of the aneurysm were carried out in seven patients with arterial aneurysms. During these operations, soft tissues of the head were incised under a local anesthesia. A hole 25 mm in diameter was cut in the cranium, and the stereotaxic apparatus together with the proposed device were installed. The patient's head was fixed rigidly. Angiography was carried out, and the site of clipping the feeding vessel (neck of the aneurysm) was determined. Under X-ray control, the proposed device with the guide rod (and then with the working rod) were moved to the vessel, and the vessel (aneurysm neck) was clipped. Control angiography was finally done and the clip released onto the vessel.

The patients tolerated the operation well. Postoperative angiography proved the reliability of the vessel clipping. There were no complications.

The patients were observed from six months to two years. The condition of the patients is satisfactory.

Although the present invention has been described in some detail by way of illustration and example for purposes of clarity of understanding, it will, of course, be understood that various changes and modifications may be made in the form, details, and arrangements of the parts without departing from the scope of the invention as set forth in the following claims.

What is claimed is:

1. A device for putting clips on vessels, comprising: a shackle; a tubular housing member having a tapered end and mounted on said shackle and being movable along an axis; a removable and threaded guide rod adapted to be inserted into the cavity of said tubular housing member for guiding said tubular housing member to the vessel to be clipped; a working rod including a tubular member, and a grip having means for holding said clip, also adapted to be inserted into the cavity of said tubular housing member; said grip being positioned within said tubular member by a spring controllable by an adjusting knob; said working rod being disposed coaxial with respect to said tubular housing member and movable along said axis; each of said working rod and said tubular housing member having threaded means and associated adjusting wheels mounted in said shackle for controlling the axial movements thereof; said adjusting wheel for said working rod also used for controlling the axial movement of said guide rod; and each of said threaded guide rod and said working rod having a rule cooperatively associated with said shackle for respectively monitoring the depth of said guide rod and for setting the point at which the jaws of said clip are opened prior to clipping and releasing said clip onto said vessel.

2. The device according to claim 1, wherein said threaded means comprising a first threaded sleeve secured on said tubular housing member and mounted in said shackle and a second threaded sleeve secured on said tubular member and adapted to be mounted on said shackle in coaxial alignment with said tubular housing member, and said adjusting wheels being in the form of threaded nuts engageable with said threaded sleeves in order to move said tubular housing member and said working rod.

3. The device according to claim 2, further including a sleeve in said shackle coaxially disposed about said first sleeve and a fixing screw located between said sleeve and said first sleeve for preventing the mutual rotation of said sleeves.

* * * * *